United States Patent [19]

Aya et al.

[11] 4,431,441
[45] Feb. 14, 1984

[54] PYRAZOLYL ACRYLATES AND HERBICIDAL USE

[75] Inventors: Masahiro Aya, Kodaira; Junichi Saito, Mitaka; Atsumi Kamochi, Hino; Koichi Moriya, Hachioji, all of Japan

[73] Assignee: Nihon Tokushu Noyaku Seizo K.K., Tokyo, Japan

[21] Appl. No.: 382,750

[22] Filed: May 27, 1982

[30] Foreign Application Priority Data

Jun. 10, 1981 [JP] Japan .................................. 56-88062

[51] Int. Cl.$^3$ .................... A01N 43/56; C07D 231/14
[52] U.S. Cl. ........................................ 71/92; 548/377
[58] Field of Search ............................ 548/377; 71/92

[56] References Cited

U.S. PATENT DOCUMENTS 4,063,925 12/1977 Konotsune et al. .................... 71/92

FOREIGN PATENT DOCUMENTS 2450821 10/1980 France .
2022375 2/1979 United Kingdom .

OTHER PUBLICATIONS

Hock et al., Chem. Abst., 1971, vol. 74, No. 30975s.
Chemical Abstracts, vol. 87, No. 3, 7/18/77, p. 653.

*Primary Examiner*—Alan L. Rotman
*Assistant Examiner*—Kurt G. Briscoe
*Attorney, Agent, or Firm*—Sprung, Horn, Kramer & Woods

[57] ABSTRACT

Pyrazole derivatives of the formula

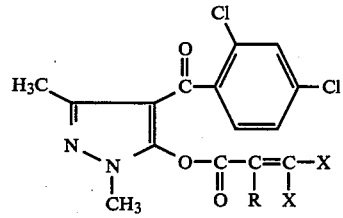

in which
X each independently is a halogen atom, and
R is a halogen atom or an aryl group optionally substituted by halogen or $C_1$ to $C_6$ alkyl,
which possess herbicidal activity.

13 Claims, No Drawings

PYRAZOLYL ACRYLATES AND HERBICIDAL USE

This invention relates to certain new pyrazole derivatives, to a process for their preparation and to their use as herbicides.

It is disclosed in Japanese Publication No. Sho 54-36648, published before the application date of this application, that the compounds of the general formula

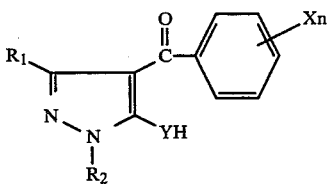

in which, $R_1$ is a hydrogen atom or a lower alkyl group, $R_2$ is a lower alkyl group, and X each independently is a halogen atom or a nitro, lower alkyl, trifluoromethyl, lower alkoxy, lower alkane sulfonyl, cyano, lower alkylthio or aliphatic acyl group, n is 1, 2, 3 or 4, and, Y represents an oxygen atom or a sulfur atom, and salts thereof or esters thereof with an organic acid selected from aliphatic, alicyclic or aromatic carboxylic acids, carbamic acids, sulfonic acids, thiophosphoric acid diesters, carbonic acid or thiocarbonic acid monoesters, dibasic acids and esters with organic acids of the general formula

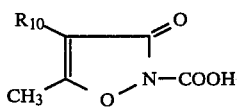

in which, $R_{10}$ represents a hydrogen atom or a halogen atom, have herbicidal activity.

The present invention now provides, as new compounds, the pyrazole derivatives of the general formula

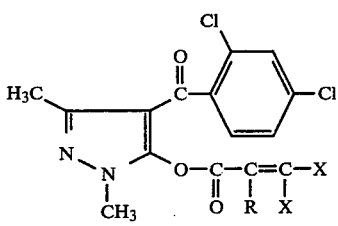

in which,

X each is a halogen atom, and

R is a halogen atom or an aryl group optionally substituted by halogen or $C_1$ to $C_6$ alkyl.

The present invention also provides a process for the preparation of a pyrazole derivative of the formula (I), in which 1,3-dimethyl-4-(2,4-dichlorobenzoyl)-5-hydroxypyrazole is reacted with an acid halide of the general formula

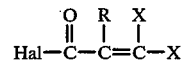

in which,

X and R have the abovementioned meanings, and

Hal represents a halogen atom.

The abovementioned prior art does not disclose the compounds of the present invention, which have the

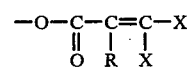

residue.

It has been discovered that the novel pyrazole derivatives of the formula (I) of the present invention have excellent herbicidal activity. Further the compounds of the present invention show an excellent herbicidal effect with a low dose compared with the compounds disclosed in the prior art. In addition it has been found that the compounds of the present invention show low toxicity to warm-blooded animals, and are well tolerated by crop plants and may therefore be applied safely. The present invention thus represents a significant contribution to the art.

The process according to the present invention may be represented by the following equation:

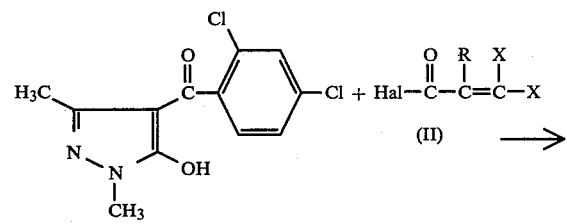

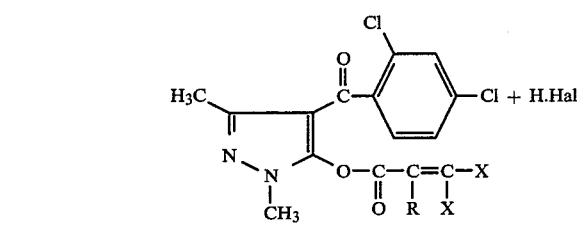

(wherein X, R and Hal have the abovementioned meanings).

Preferred compounds according to the present invention and preferred starting materials of formula (II) are those in which X represents halogen atoms such as a fluorine, chlorine, bromine, or iodine atom, and R represents a halogen atom such as those mentioned above, or an aryl group, such as phenyl or naphthyl, optionally substituted by a halogen atom such as those mentioned above or a $C_1$ to $C_6$ alkyl group such as methyl, ethyl, propyl, isopropyl or n-, iso-, sec.-, or tert.-butyl.

Particularly preferred compounds and starting materials are those in which X represents chlorine atoms and those in which R represents a chlorine atom or a phenyl, naphthyl, monochloro-substituted phenyl- or o-, m- or p-tolyl. An especially preferred compound is the compound in which X and R both represent chlorine atoms.

Examples of preferred acid halides of the general formula (II) for use as starting material in the process of the present invention, are as follows: 3,3-dichloro-2-phenyl acrylic acid chloride, 3,3-dichloro-2-p-tolyl acrylic acid chloride, 3,3-dichloro-2-m-tolyl acrylic acid chloride, 3,3-dichloro-2-o-tolyl acrylic acid chloride, 3,3-dichloro-2-p-chlorophenyl acrylic acid chloride, 3,3-dichloro-2-α-naphthyl acrylic acid chloride, trichloro acrylic acid chloride, and, in addition, the other corresponding halides, preferably bromides.

If 1,3-dimethyl-4-(2,4-dichlorobenzoyl)-5-hydroxypyrazole and 3,3-dichloro-2-phenyl acrylic acid chloride are used as starting materials, the process according to the present invention is illustrated by the following equation:

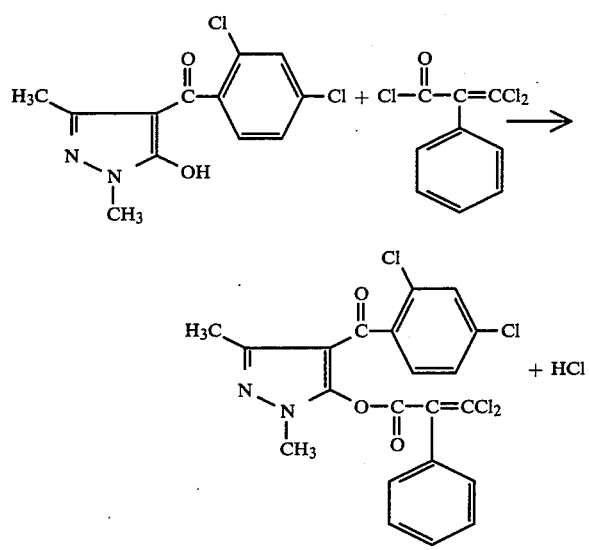

The process of the present invention is preferably carried out in the presence of a solvent or diluent. For this purpose, any of the inert solvents or diluents may be employed. The following may be mentioned as examples of suitable solvents or diluents for use according to the present invention:

water, aliphatic, cycloaliphatic and aromatic hydrocarbons optionally chlorinated in each case (for example hexane, cyclohexane, petroleum ether, ligroin, benzene, toluene, xylene, methylene chloride, chloroform, carbontetrachloride, ethylene chloride, trichloroethylene and chlorobenzene), ethers (for example dimethyl ether, methyl ethyl ether, di-isopropyl ether, dibutyl ether, propylene oxide, dioxane and tetrahydrofuran), ketones (for example acetone, methyl ethyl ketone, methyl isopropyl ketone and methyl isobutyl ketone), nitriles (for example acetonitrile, propionitrile and acrylonitrile), esters (for example ethyl acetate and amyl acetate), acid amides (for example dimethylformamide and dimethylacetamide), sulfones, sulfoxides (for example dimethylsulfoxide), sulfolane and bases (for example pyridine).

The process of the present invention may be carried out in the presence of an acid-binding agent such as a hydroxide of an alkali metal, a carbonate, a bicarbonate, an alcoholate, a tertiary amine (for example triethylamine), diethylaniline or pyridine.

The process of the present invention may be carried out within a wide temperature range, for example, a temperature between $-20°$ C. and the boiling point of the reaction mixture, and preferably at a temperature between $0°$ C. to $100°$ C. The reaction is preferably carried out at atmospheric pressure, but may be carried out under reduced or elevated pressure.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

It should be pointed out that the compounds according to the present invention show excellent selectivity to paddy rice under flood condition. The compounds of this invention are effective for the control of wide varieties of paddy weeds, for example:

the dicotyledon weeds *Rotala indica, Lindernia pyxidaria, Ludwiga prostrata, Potamogeton distinctus* and *Elatine triandra;* and the monocotyledon weeds *Echinochloa crus-galli, Monochoria vaginalis, Eleocharis acicula-* ris, Eleocharis Kuroguwai, Cyperus serotinus, Sagittaria pygmaea, Alisma canaliculatum, and Scirpus juncoides.

Further compounds of the present invention also show particular herbicidal activity for the control of the following upland weeds:

the dicotyledon weeds Polygonum sp., *Chenopodium album, Stellaria media* and *Portulaca oleracea;* and the monocotyledon weeds *Echinochloa crus-galli, Digitaria adscendens* and *Cyperus iria.*

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, as well as ULV cold mist and warm mist formulations.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acids esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.001 to 100 percent by weight of active compound, preferably from 0.005 to 95 percent by weight.

The active compounds according to the invention can be present in the formulations, or in the various use forms, in combination with other active compounds, such as fungicides, bactericides, insecticides, nematicides, herbicides, bird repellents, growth factors, plant nutrients and agents for improving soil structure.

The active compounds can be used as such, as their formulations or as the use forms prepared therefrom, such as ready-to-use solutions, emulsions, suspensions, powders, pastes and granules. They may be used in the customary manner, for example by spraying, atomizing, dusting, scattering and watering.

It is also possible to apply the active compounds by means of the ultra-low-volume method, whereby it is possible to employ the compounds at a concentration of up to 100%. The active compounds can also be incorporated into the soil.

In actual use the content of active compounds in said various formulations or ready-to-use preparations is generally from 0.01 to 95% by weight and preferably from 0.05 to 60% by weight.

The amount of an active compound can vary within a substantial range. It depends essentially on the nature of the desired effect. In general amounts used are between 0.1 to 2.0 kg of active compound per hectare, preferably between 0.25 and 2 kg per hectare.

The present invention also provides herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The following example illustrates the processes for the production of compounds of the present invention.

EXAMPLE 1

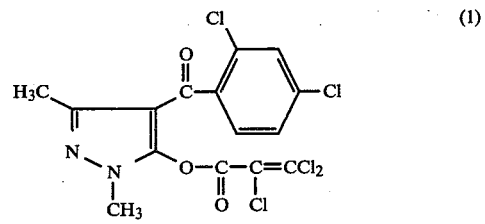

2.85 g of 1,3-dimethyl-4-(2,4-dichlorobenzoyl)-5-hydroxy pyrazole and 1.01 g of triethylamine were dissolved in 20 ml of benzene. 1.94 g of trichloroacrylic acid chloride were dropped into the solution. The reaction mixture was stirred for 3 hours at the reflux temperature of benzene. After the completion of the reaction, water was added to the reaction mixture, the organic layer was separated and dried. Benzene was distilled off under reduced pressure to give 3.3 g of 1,3-dimethyl-4-(2,4-dichlorobenzoyl)-5-trichloroacryloyloxy pyrazole as colorless crystals of melting point 141° to 142° C.

The compounds of the present invention shown in Table 1 were prepared in a manner analogous to that described above.

TABLE 1

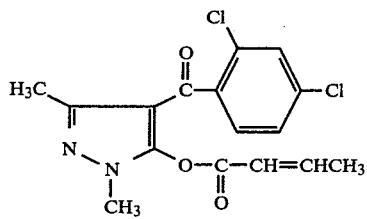

| Compound No. | X | R | Physical constant m.p. °C. |
|---|---|---|---|
| 2 | Cl | –⌬ (phenyl) | 136–138.5 |
| 3 | Cl | –⌬–CH₃ | 119–120 |
| 4 | Cl | –⌬ (o-CH₃ phenyl) | 118–119 |
| 5 | Cl | –CH₂–⌬ (benzyl) | 107–108 |
| 6 | Cl | –⌬–Cl | 152–154 |
| 7 | Cl | –⌬⌬ (naphthyl) | 103–106 |

The compositions according to the invention and the herbicidal activity of the compounds of the present invention are illustrated by the following examples.

In these examples, the compounds according to the present invention are each identified by the number (given in brackets) from Example 1 and Table 1.

Parts and ratios given are by weight.

The known comparison compounds are identified as follows:

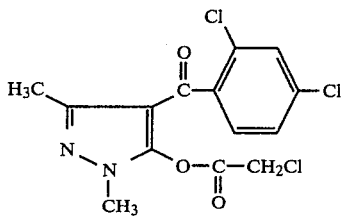
(A-1)

(a compound disclosed in the Japanese Published Patent Application No. 36648/79), (A-2)

(a compound disclosed in the Japanese Published Patent Application No. 36648/79).

EXAMPLE 2

A wettable powder was prepared by grinding and mixing 15 parts of the compound (1), 80 parts of a mixture consisting of diatomomaceous powder and clay powder (1:5), 2 parts of sodium alkylbenzene sulfonate, 3 parts of a condensate of sodium alkylnaphthalene sulfonate and formalin. This was diluted with water before spraying.

EXAMPLE 3

An emulsion was prepared by mixing and stirring 15 parts of the compound (2), 70 parts of xylene, 8 parts of polyoxyethylene alkyl phenyl ether, 7 parts of calcium alkylbenzene sulfonate. This was diluted with water before spraying.

EXAMPLE 4

A powder for use as a dusting agent was prepared by grinding and mixing 2 parts of the compound (3) and 98 parts of clay powder.

EXAMPLE 5

A powder for use as a dusting agent was prepared by grinding and mixing 1.5 parts of the compound (4), 0.5 part of isopropyl hydrogenphosphate (PAP) and 98 parts of clay powder.

EXAMPLE 6

Granules were prepared by adding 25 parts of water to a mixture consisting of 10 parts of the compound (5), 30 parts of bentonite (montmorillonite), 58 parts of talc and 2 parts of lignin sulfonate, kneading and granulating by means of a extrusion granulator to produce granules having a granule size between 10 and 40 mesh and drying at from 40° to 50° C. The granules obtained were applied by scattering.

EXAMPLE 7

Granules were prepared by adding 75 parts of mineral granules having from 0.2 to 2 mm particle size distribution to a rotary mixer, spraying onto the granules 7 parts of the compound (7) dissolved in an organic solvent with rotating said mixer so as to moisten the granules homogeneously, and drying at from 40° to 50° C. The granules obtained were applied by scattering.

EXAMPLE 8

Treatment for the control of paddy weeds under flood condition (Pot Test)

Preparation of an active composition

Solvent: 5 parts by weight of acetone
Emulsifier: 1 part by weight of benzyloxy polyglycol ether A preparation of the active compound was obtained as an emulsifiable concentrate by mixing 1 part by weight of the active compound with the aforesaid amounts of the solvent and emulsifier. A predetermined amount of the preparation was obtained by dilution with water.

TEST PROCEDURE

Wagner pots (1/5,000 are) were filled with paddy field soil and then irrigated. Two rice seedlings (variety: Kinmaze) at the 2-3 leaf stage (plants about 10 cm in height) were transplanted in each pot. After transplanting, seeds of rice, *Echinochloa crus-galli*, *Monochoria vaginalis*, *Soirpus juncoides*, *Cyperus difformis* and broad-leaved weeds were sown and rhizome of *Eleocharis acicularis* and tubers of *Sagittaria pygmaea* were planted. When the *Echinochloa crus-galli* had grown to approximately the 2 leaf stage (about 7 to 9 days after the sowing), the pots were filled with water to a depth of about 6 cm, and a predetermined amount of the active compound in the form of an emulsion was applied into the water using pipette. The water in the pots was leaked out in a rate of 2 cm/day for 2 days following treatment. 4 weeks after the treatment the herbicidal efficacy and the degree of phytotoxicity were evaluated on a scale of from 0 to 10 in accordance with the following standards.

The herbicidal efficacy was evaluated as follows in comparison with an untreated control:

| Rating | Weed-kill ratio based on the control |
|---|---|
| 10: | 100% (withered) |
| 9: | at least 90% but less than 100% |
| 8: | at least 80% but less than 90% |
| 7: | at least 70% but less than 80% |
| 6: | at least 60% but less than 70% |
| 5: | at least 50% but less than 60% |
| 4: | at least 40% but less than 50% |
| 3: | at least 30% but less than 40% |
| 2: | at least 20% but less than 30% |
| 1: | at least 10% but less than 20% |
| 0: | less than 10% (not effective) |

The phytotoxicity towards the crop was evaluated as follows in comparison with the untreated control:

| Rating | Phytotoxicity rate in comparison with the control |
|---|---|
| 10: | at least 90% (fatal damage) |
| 9: | at least 80% but less than 90% |
| 8: | at least 70% but less than 80% |
| 7: | at least 60% but less than 70% |
| 6: | at least 50% but less than 60% |
| 5: | at least 40% but less than 50% |
| 4: | at least 30% but less than 40% |
| 3: | at least 20% but less than 30% |
| 2: | at least 10% but less than 20% |
| 1: | more than 0 but less than 10% |
| 0: | 0% (no phytotoxicity) |

The test results are shown in Table 2 in which the symbols a to g represent the following weeds:

| a: | *Echinochloa crus-galli* |
|---|---|
| b: | *Eleocharis acicularis* |
| c: | *Cyperus difformis* |
| d: | *Scirpus juncoides* |
| e: | *Monochoria vaginalis* |
| f: | *Sagittaria pygmaea* |
| g: | Broad-leaved weeds (*Lindernia pyxidaria, Rotala indica, Elatine triandra*) |

TABLE 2

| Compound No. | Effective dose kg/ha | herbicidal activity Weed | | | | | | | harmful effect Crop* | |
|---|---|---|---|---|---|---|---|---|---|---|
| | | a | b | c | d | e | f | g | r-1 | r-2 |
| 1 | 1.0 | 10 | 10 | 10 | 10 | 10 | 10 | 10 | 0 | 0 |
|   | 0.5 | 10 | 10 | 10 | 10 | 10 | 10 | 10 | 0 | 0 |
|   | 0.25 | 9 | 9 | 10 | 9 | 10 | 10 | 9 | 0 | 0 |
| 2 | 1.0 | 10 | 10 | 10 | 10 | 10 | 10 | 10 | 0 | 0 |
|   | 0.5 | 9 | 10 | 10 | 10 | 10 | 10 | 10 | 0 | 0 |
|   | 0.25 | 9 | 10 | 10 | 10 | 10 | 9 | 9 | 0 | 0 |
| 3 | 1.0 | 10 | 10 | 10 | 10 | 10 | 10 | 10 | 0 | 0 |
|   | 0.5 | 10 | 10 | 10 | 10 | 10 | 10 | 10 | 0 | 0 |
|   | 0.25 | 9 | 9 | 10 | 9 | 10 | 10 | 10 | 0 | 0 |
| 4 | 1.0 | 10 | 10 | 10 | 10 | 10 | 10 | 10 | 0 | 0 |
|   | 0.5 | 9 | 10 | 10 | 10 | 10 | 10 | 10 | 0 | 0 |
|   | 0.25 | 9 | 9 | 10 | 9 | 10 | 9 | 9 | 0 | 0 |
| 5 | 1.0 | 10 | 10 | 10 | 10 | 10 | 10 | 10 | 0 | 0 |
|   | 0.5 | 9 | 10 | 10 | 10 | 10 | 10 | 10 | 0 | 0 |
|   | 0.25 | 9 | 9 | 10 | 10 | 10 | 10 | 9 | 0 | 0 |
| 6 | 1.0 | 10 | 10 | 10 | 10 | 10 | 10 | 10 | 0 | 0 |
|   | 0.5 | 9 | 9 | 10 | 9 | 9 | 9 | 10 | 0 | 0 |
|   | 0.25 | 8 | 9 | 10 | 9 | 8 | 9 | 9 | 0 | 0 |
| 7 | 1.0 | 10 | 10 | 10 | 10 | 10 | 10 | 10 | 0 | 0 |
|   | 0.5 | 9 | 9 | 10 | 9 | 10 | 10 | 10 | 0 | 0 |
|   | 0.25 | 9 | 9 | 10 | 8 | 9 | 9 | 9 | 0 | 0 |
| Comparison A-1 | 1.0 | 8 | 5 | 8 | 8 | 8 | 6 | 8 | 0 | 0 |
|   | 0.5 | 5 | 1 | 5 | 5 | 5 | 3 | 4 | 0 | 0 |
|   | 0.25 | 2 | 0 | 2 | 2 | 2 | 1 | 2 | 0 | 0 |
| Comparison A-2 | 1.0 | 8 | 5 | 7 | 7 | 8 | 5 | 8 | 0 | 0 |
|   | 0.5 | 3 | 1 | 2 | 2 | 4 | 1 | 4 | 0 | 0 |
|   | 0.25 | 1 | 0 | 1 | 1 | 1 | 0 | 1 | 0 | 0 |

*Symbols in the crop column have the following meaning
r-1: transplanted rice plant
r-2: growing rice plant.

It will be understood that the specification and examples are illustrative but not limitative of the present invention and that other embodiments within the spirit and scope of the invention will suggest themselves to those skilled in the art.

We claim:

1. A pyrazole derivative of the formula

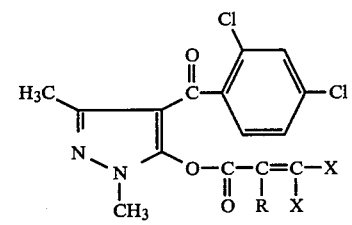

in which
X each independently is a halogen atom, and
R is a halogen atom or a phenyl or naphthyl group optionally substituted by halogen or $C_1$ to $C_6$ alkyl.

2. A pyrazole derivative according to claim 1, in which X is a fluorine, chlorine, bromine or iodine atom, and R is a fluorine, chlorine, bromine or iodine atom or a phenyl or naphthyl group optionally substituted by fluorine, chlorine, bromine, iodine, methyl, ethyl, propyl, isopropyl, n-, iso-, sec- or tert-butyl.

3. A pyrazole derivative according to claim 1, wherein each X is a chlorine atom and R is a chlorine atom or a phenyl, naphthyl, monochloro substituted phenyl or o-, m-, or p-tolyl group.

4. A compound according to claim 1, wherein such compound is 1,3-dimethyl-4-(2,4-dichlorobenzoyl)-5-trichloroacryloyloxy pyrazole of the formula

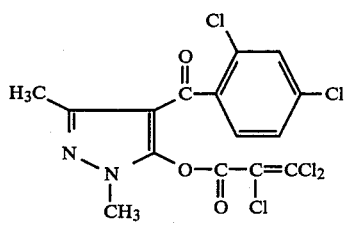

5. A compound according to claim 1, wherein such compound is 1,3-dimethyl-4-(2,4-dichlorobenzoyl)-5-(α-phenyl-dichloroacryloyloxy)-pyrazole of the formula

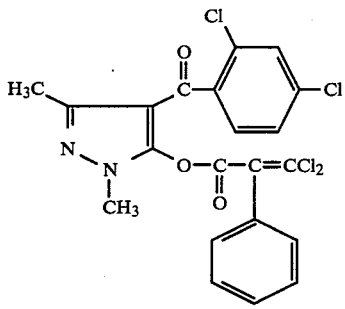

6. A compound according to claim 1, wherein such compound is 1,3,-dimethyl-4-(2,4-dichlorobenzoyl)-5-(α-p-tolyl-dichloroacryloyloxy)-pyrazole of the formula

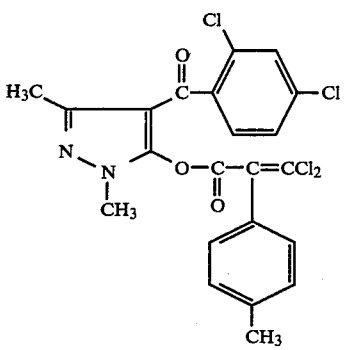

7. A compound according to claim 1, wherein said compound is 1,3-dimethyl-4-(2,4-dichlorobenzoyl)-5-(α-m-tolyl-dichloroacryloyloxy)-pyrazole of the formula

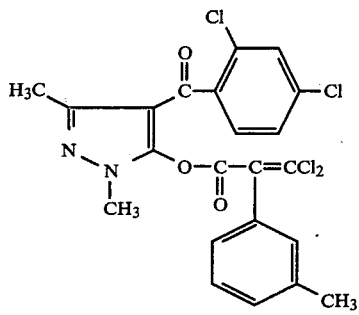

8. A compound according to claim 1, wherein such compound is 1,3-dimethyl-4-(2,4-dichlorobenzoyl)-5-(α-o-tolyl-dichloroacryloyloxy)-pyrazole of the formula

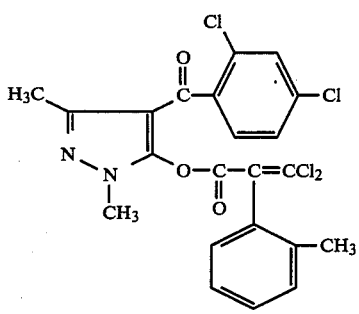

9. A compound according to claim 1, wherein such compound is 1,3-dimethyl-4-(2,4-dichlorobenzoyl)-5-(α-p-chlorophenyl-dichloroacryloyloxy)-pyrazole of the formula

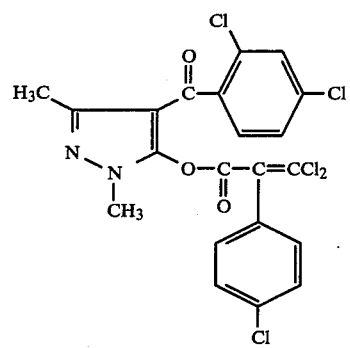

10. A compound according to claim 1, wherein such compound is 1,3-dimethyl-4-(2,4-dichlorobenzoyl)-5-(α-napth-1-yl-dichloroacryloyloxy)-pyrazole of the formula

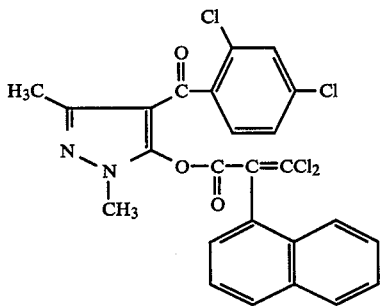

11. A herbicidal composition comprising a herbicidally effective amount of a compound according to claim 1 in admixture with a diluent.

12. A method of combating weeds comprising applying to the weeds, or to a habitat thereof, a herbicidally effective amount of a compound according to claim 1.

13. A method according to claim 12, wherein such compound is 1,3,-dimethyl-4-(2,4-dichlorobenzoyl)-5-trichloroacryloyloxy pyrazole, 1,3-dimethyl-4-(2,4-dichlorobenzoyl)-5-(αphenyl-dichloroacryloyloxy)-pyrazole, 1,3,-dimethyl-4-(2,4-dichlorobenzoyl)-5-(α-p-tolyl-dichloroxoacryloxyoxy)-pyrazole, 1,3-dimethyl-4-(2,4-dichlorobenzoyl)-5-(α-m-tolyl-dichloroacryloyloxy)-pyrazole, 1,3-dimethyl-4-(2,4-dichlorobenzoyl)-5-(α-o-tolyl-dichloroacryloyloxy)-pyrazole, 1,3-dimethyl-4-(2,4-dichlorobenzoyl)-5-(α-p-chlorophenyl-dichloroacryloyloxy)-pyrazole, or 1,3-dimethyl-4-(2,4-dichlorobenzoyl)-5-(α-napth-1-yl-dichloroacryloyloxy)-pyrazole.

* * * * *